(12) United States Patent
Medoff et al.

(10) Patent No.: US 9,428,479 B2
(45) Date of Patent: Aug. 30, 2016

(54) CONVERSION OF BIOMASS

(71) Applicant: Xyleco, Inc., Woburn, MA (US)

(72) Inventors: Marshall Medoff, Brookline, MA (US); Thomas Craig Masterman, Brookline, MA (US); Christopher Cooper, Rehoboth, MA (US); Jihan Khan, Cambridge, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

(21) Appl. No.: 13/934,704

(22) Filed: Jul. 3, 2013

(65) Prior Publication Data

US 2014/0011248 A1 Jan. 9, 2014

Related U.S. Application Data

(60) Provisional application No. 61/667,481, filed on Jul. 3, 2012.

(51) Int. Cl.

| *C07D 307/68* | (2006.01) |
| *C08H 8/00* | (2010.01) |
| *C07D 307/12* | (2006.01) |
| *C07D 307/50* | (2006.01) |
| *C07D 307/08* | (2006.01) |
| *C07D 307/44* | (2006.01) |

(52) U.S. Cl.
CPC ............ *C07D 307/68* (2013.01); *C07D 307/08* (2013.01); *C07D 307/12* (2013.01); *C07D 307/44* (2013.01); *C07D 307/50* (2013.01); *C08H 8/00* (2013.01)

(58) Field of Classification Search
CPC .................................................. C07D 307/68
USPC .......... 435/41, 136, 161; 549/429, 498, 503, 549/506
See application file for complete search history.

(56) References Cited

U.S. PATENT DOCUMENTS

| 4,261,905 | A | * | 4/1981 | Preobrazhenskaya et al. ............................ 549/503 |
| 7,019,155 | B2 | | 3/2006 | Manzer |
| 7,932,065 | B2 | | 4/2011 | Medoff |
| 2004/0173533 | A1 | * | 9/2004 | Farone et al. ................ 210/656 |
| 2007/0077630 | A1 | | 4/2007 | Harris et al. |
| 2008/0313954 | A1 | | 12/2008 | Lee et al. |
| 2009/0286295 | A1 | * | 11/2009 | Medoff et al. ................ 435/162 |
| 2010/0064746 | A1 | * | 3/2010 | Medoff ............... 71/8 |
| 2010/0069626 | A1 | | 3/2010 | Kilambi |
| 2010/0087687 | A1 | * | 4/2010 | Medoff .......... 568/840 |
| 2010/0124772 | A1 | | 5/2010 | Sabesan |
| 2010/0297705 | A1 | | 11/2010 | Medoff et al. |
| 2011/0022840 | A1 | | 1/2011 | Stefan et al. |
| 2011/0063500 | A1 | | 3/2011 | Loher et al. |
| 2011/0107659 | A1 | | 5/2011 | Gruter et al. |
| 2011/0177559 | A1 | | 7/2011 | Medoff et al. |
| 2012/0003704 | A1 | | 1/2012 | Medoff |
| 2012/0309060 | A1 | | 12/2012 | Medoff |

FOREIGN PATENT DOCUMENTS

WO 2011063500 6/2011

OTHER PUBLICATIONS

Moreau et al. (1998). Selective preparation of furfural from xylose over microporous solid acid catalysts. Industrial Crops and Products, v7, p. 95-99.*
Dias et al. (2007). Modified versions of sulfated zirconia as catalysts for the conversion of xylose to furfural. Catalysis Letters, v114(3-4), p. 151-160.*
Moiser et al. (2005). Features of promising technologies for pretreatment of lignocellulosic biomass. Bloresource Technology, v96, p. 673-686.*
Kang et al. (2004). Production of cellulases and hemicellulases by Aspergillus niger KK2 from lignocellulosic biomass. Bioresource Technology, v91, p. 153-156.*
Carter et al. (epub Mar. 31, 2011). Removal and Recovery of Furfural, 5-Hydroxymethylfurfural, and Acetic Acid From Aqueous Solutions Using a Soluble Polyelectrolyte. Biotechnology and Bioengineering, v108(9), p. 2046-2052.*
Palmqvist et al. (2008). Fermentation of lignocellulosic hydrolysates. II: inhibitors and mechanisms of inhibition. Bioresource Technology, v74, p. 25-33.*
Sluiter et al. (2010). Compositional Analysis of Lignocellulosic Feedstocks. 1. Review and Description of Methods. J Agric Food Chem, v58, p. 9043-9053.*
Tao et al. (epub Dec. 13, 2010). Efficient process for the conversion of xylose to furfural with acidic ionic liquid. Can. J. Chem, v89, p. 83-87.*
Wooley et al. (1998). A Nine-Zone Simulating Moving Bed for the Recovery of Glucose and Xylose from Biomass Hydrolyzate. Ind Eng Chem Res, v37(9), p. 3699-3709.*
Choudhary et al. Xylose Isomerization to Xylulose and its Dehydration to Furfural in Aqueous Media. ACS Catalysis (Nov. 2011), v1, p. 1724-1728.*
PCT Search Report—Corresponding PCT Application No. PCT/US2013/049265—Dec. 23, 2013—3 pages.
Search Report issued by Intellectual Property Office of Singapore for Application No. 11201407774X dated Oct. 29, 2015 (3 pages).

* cited by examiner

*Primary Examiner* — Scott Long
*Assistant Examiner* — Sean C Barron
(74) *Attorney, Agent, or Firm* — Wilmer Cutler Pickering Hale and Dorr LLP

(57) ABSTRACT

Biomass feedstocks (e.g., plant biomass, animal biomass, and municipal waste biomass) are processed to produce useful products, such as fuels. For example, systems are described that can convert feedstock materials to a sugar solution, especially, xylose, which can then be chemically converted to furfural and furfural-derived products.

24 Claims, 3 Drawing Sheets

CONVERSION OF BIOMASS

RELATED APPLICATIONS

This application claims priority to U.S. Provisional Application Ser. No. 61/667,481, filed Jul. 3, 2012. The complete disclosure of this provisional application is hereby incorporated by reference herein.

BACKGROUND OF THE INVENTION

Various carbohydrates, such as cellulosic and lignocellulosic materials, e.g., in fibrous form, are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,846,295, 7,307,108, 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, "FIBROUS MATERIALS AND COMPOSITES," U.S. Patent Publication No. 2007/0045456 AND "SACCHARIFYING BIOMASS", U.S. patent application Ser. Nos. 12/704,515. 12/417,720.

SUMMARY

Generally, this invention relates to processes for converting a cellulosic, starchy or lignocellulosic feedstock to useful products, organic sugar derived products for example, furfural and furfural-derived products.

Xylose can be chemically converted into many useful intermediates and products. The intermediates and products include but are not limited to furfural, furfuryl alcohol, methyl furan, methyl tetrahydrofuran, furan, tetrahydrofuran and similar structures. Xylose is shown in its hemiacetal structure as I. Xylose can exist in various different chemical forms.

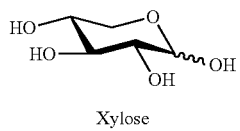

Xylose

I

The conversion can be by chemically converting the xylose the product or the intermediate. The xylose can be chemically converted, for example, by any one or more of cyclization reactions, polymerization reactions, condensation reactions, reduction reactions, oxidation reactions, esterification reactions, alkylation reactions, and combinations thereof. The product of the conversion can be, for example, furfural. Optionally, the product and the intermediates can be isolated (e.g., by chromatography, crystallization, precipitation, filtering, centrifugation, evaporation, extraction, distillation, phase separation, heating, vacuum distillation or combinations of these).

For instance, in the case of chemically converting xylose to furfural; furfural can be a product or an intermediate that can be, in turn, converted to wide array of products including but not limited to furfuryl alcohol, methyl furan, furan, methyl tetrahydrofuran and tetrahydrofuran. In some cases, converting can be by reacting the xylose or the chemical intermediate with an acid catalyst. Thus, for example, xylose can be dehydrated, losing 3 moles of water, to give furfural and the furfural can be hydrogenated to furfuryl alcohol. Optionally, the acid catalyst can be selected for example from acidified Zeolites, acidified silica, surface grafted silicas, acid clays, functionalized mesoporous silicas, poly acids, acid functionalized polymers, poly sulfonic acids, Nafion® perfluorinated sulfonic acid resin or membrane, poly acetic acids, poly phosphonic acids, polystyrene sulfonic acids, tetraorthosilicates, 3-(mercaptopropyl) trimethoxysilane, Lewis acids, microporous silicoaluminaphosphate, metal oxides, $ZrO_2$, $Al_2O_3$, $TiO_2$, $SiO_2$, $V_2O_3$, sulfate salts, $(NH_4)_2SO_4$, metal halides, $MgCl_2$, $LaCl_3$, $FeCl_3$, metal carbonates, $Cs_2CO_3$, ionic liquids, Tungsten oxides, Tungstate, Phosphoric acid, Phosphonic acid, sulfuric acid, hydrochloric acid, nitric acid and combinations thereof.

In some cases, the methods include heating the xylose (e.g., to at least 50° C., at least 60° C., at least 70° C., at least 80° C. at least 90° C., at least 100° C., at least, 120° C. at least 140° C., at least 160° C., at least 180° C., at least 200° C., at least 220° C., at least 240° C., at least 260° C. or at least 280° C. or at least 300° C., e.g., between 200 and 320° C., between 250 and 300° C., between 260 and 290° C.), and/or subjecting the same to greater than atmospheric pressure (e.g., at least 10 psi, at least 100 psi, at least 500 psi, at least 1000 psi, at least 5000 psi, at least 12000 psi, e.g., between 10 and 12000 psi). The pressure can be derived from the autogenous pressure generated by temperatures, but also by added pressure from added gases such as nitrogen.

In some aspects xylose is transformed, e.g., chemically, to a furfural-derived product. For example, transforming can comprise a chemical reaction selected from the group consisting of, a reduction reaction, a decarbonylation reaction, a de-aromatization reaction, a polymerization reaction or combinations thereof. The furfural-derived product can be furfuryl alcohol, methytetrahydrofuran, furan, tetrahydrofuran, furancarboxaldehyde, poly(furfuryl alcohol), a polyether or combinations of these. The products include all possible stereoisomers including those that can be obtained by chemical conversions of prochiral centers. For example, the conversion of furfuryl alcohol to tetrahydrofurfuryl alcohol results in a product with a stereocenter at the alpha carbon. Thus, both stereoisomers can be made.

The processes disclosed herein include saccharification of the feedstock, and transportation of the feedstock from a remote location, e.g., where the feedstock is produced or stored, to the manufacturing facility. In some cases, saccharification can take place partially or entirely during transport. In some implementations, the process further includes reducing the recalcitrance of the feedstock, before or during saccharification. The process may include the further steps of measuring the lignin content of the feedstock and determining whether pretreatment is needed and under what conditions based on the measured lignin content.

Many of the methods described herein can provide cellulosic and/or lignocellulosic materials that have, for example, a lower recalcitrance level, a lower molecular weight, a different level of functionalization and/or crystallinity relative to a native material. Many of the methods provide materials that can be more readily utilized by a variety of microorganisms, such as one or more homoacetogens or heteroacetogens (with or without enzymatic hydrolysis assistance) to produce useful products, such as energy, fuels, foods, sugars (e.g., xylose and glucose), organic products (e.g., derived from sugars), and materials. In addition, to the furfural product describe above examples of products that can be derived from sugars include, but are not limited to, polyethers, hydrogen, alcohols (e.g., monohydric alcohols or dihydric alcohols, such as ethanol, n-propanol, iso-propanol, propylene glycol, 1,4-butanediol, 1,3-propanediol, methyl or ethyl esters of any of these alcohols), biodiesel, organic acids (e.g., acetic acid and/or lactic acid), hydrocarbons, co-products (e.g., proteins, such as cellulolytic proteins (enzymes) or single cell proteins), and mixtures of any of these. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid and olefins, such as ethylene. Other products include methyl acrylate, methyl methacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. application Ser. No. 12/417,723, filed Apr. 3, 2009; the full disclosure of which is hereby incorporated by reference herein in its entirety.

Some of the products obtained by the methods disclosed herein, can be used directly or as a chemical intermediate to a solvent (e.g., for refining lubricating oils), as a fungicide, as a weed killer, as transportation fuels, nylon, lubricants, solvents, adhesives, medicines, resin and plastics. Many of the products obtained by the methods disclosed herein, such as ethanol or n-butanol, can be utilized directly as a fuel or as a blend with other components, such as gasoline, for powering cars, trucks, tractors, ships or trains, e.g., as an internal combustion fuel or as a fuel cell feedstock. Other products (e.g., organic acids, such as acetic acid and/or lactic acid) can be converted to other moieties (e.g., esters or anhydrides) that can be converted and utilized as a fuel. Many of the products obtained can also be utilized to power watercraft and aircraft, such as planes, e.g., having jet engines, or helicopters. In addition, the products described herein can be utilized for electrical power generation, e.g., in a conventional steam generating plant or in a fuel cell plant.

In one aspect, the invention features a method including providing a cellulose, hemicellulose and/or lignocellulose-containing feedstock (e.g., a biomass that includes polysaccharides of glucose, xylose and other saccharides), mixing the feedstock with a solvent, such as water, and an agent, such as a saccharifying enzyme or acid, and optionally transporting the resulting mixture. Suitable acids include mineral acids, e.g., sulfuric acid or hydrochloric acid.

In one aspect, the invention features a method for converting a sugar, including converting xylose to a product or intermediate, the xylose being obtained by treating biomass with any one or more of sonication, irradiation, pyrolysis, oxidation, and saccharification. For example the biomass can be irradiated and then saccharified.

The invention can feature xylose that is derived from the treated material by a process including hydrolysis of the treated material. Hydrolysis can include contacting the treated biomass material with at least one of an acid, a base, heat, microwave energy, sonic energy, mechanical energy, shearing, milling or an enzyme. For example, the xylose can be derived from contacting material treated with at least one of oxidation, sonication, irradiation, pyrolysis and/or with at least one xylanase.

The methods can include producing glucose. Optionally the glucose and xylose are separated prior to converting the xylose to a product. Also optionally, the glucose can be fermented and then the xylose converted to an intermediate or a product.

The biomass used in the methods herein described can include hemicellulose (e.g., xylan, glucuronoxylan, arabinoxylan, glucomannan and xyloglucan). The biomass can be selected from one or more of paper, paper products, paper waste, wood, particle board, sawdust, agricultural waste, sewage, silage, grasses, wheat straw, rice hulls, bagasse, cotton, jute, hemp, flax, bamboo, sisal, abaca, straw, corn cobs, corn stover, alfalfa, hay, coconut hair, seaweed, algae, and mixtures thereof.

In some aspects the method includes irradiating the biomass prior to saccharification with between 10 and 200 Mrad. Optionally, the irradiating can be 10 and 75 Mrad, or 20 and 50 Mrad. Additionally, the irradiation is provided by an electron beam (e.g., from an electron accelerator), for example, with an electron beam power between 0.5 and 10 MeV (e.g., 0.5-2 MeV). Typical electron beam irradiation device power can be 50 kW to 500 kW, or 75 kW to 250 kW.

The method can also include reducing the recalcitrance of the feedstock prior to mixing the feedstock with the solvent and enzyme, e.g., by treating the feedstock with a physical treatment. The physical treatment can be, for example, selected from the group consisting of mechanical treatment, radiation, sonication, pyrolysis, oxidation, steam explosion, chemical treatment, and combinations thereof. Chemical treatment may include the use of a single chemical or two or more chemicals. Mechanical treatments include, for example, cutting, milling, pressing, grinding, shearing and chopping. Milling may include, for example, ball milling, hammer milling, or other types of milling.

The physical treatment can comprise any one or more of the treatments disclosed herein, applied alone or in any desired combination, and applied once or multiple times. In some cases, the physical treatment can comprise irradiating with ionizing radiation, alone or accompanied by mechanical treatment before and/or after irradiation. Irradiation can be performed, for example, with an electron beam.

In some cases, the method includes mechanically treating the feedstock to reduce the bulk density of the feedstock and/or increase the surface area of the feedstock, e.g., by performing a shearing process on the feedstock. In some embodiments, after mechanical treatment the material has a bulk density of less than 0.6 g/cm$^3$, 0.5 g/cm$^3$, 0.4 g/cm$^3$ 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, irradiated or mechanically treated or untreated biomass can be densified to 0.15 to 0.8 g/cm$^3$, 0.25 to 0.7 g/cm$^3$ or 0.25 to 0.6 g/cm$^3$.

In yet another aspect, the invention features a sugar concentrate made by saccharifying a dispersion that includes between about 10 percent by weight and about 90 percent by weight of a cellulosic or lignocellulosic material and converting this to another intermediate or product (e.g., furfural and furfural derived products).

In some implementations, one or more components of the processing equipment, for example the mechanical treatment equipment, chemical (e.g., acid or base) treatment equipment, irradiating equipment, sonicating, pyrolyzing, oxidizing, steam exploding, saccharifying and/or fermenting equipment, or any of the other equipment described herein, may be portable, e.g., in the manner of the mobile processing equipment described in U.S. patent application Ser. No. 12/374,549, and Published International Application No. WO 2008/011598, the full disclosures of which are incorporated herein by reference.

Changing a molecular structure of a material or molecules (e.g., molecules that are part of the material), as used herein, means to change the chemical bonding arrangement or conformation of the structure. For example, the change in the molecular structure can include changing the supramolecular structure of the material, oxidation of the material or molecule (e.g., adding oxygen or removing hydrogen), reduction of the material or molecules (e.g., hydrogenation), decarbonylation of a material or molecule, changing an average molecular weight, changing an average crystallinity, changing a surface area, changing a degree of polymerization, changing a porosity, changing a degree of branching, grafting on other materials, changing a crystalline domain size, or changing an overall domain size. A change in molecular structure may be effected using any one or more of the physical treatments described herein, alone or in any combination, applied once or repeatedly.

DETAILED DESCRIPTION

Figure 1:
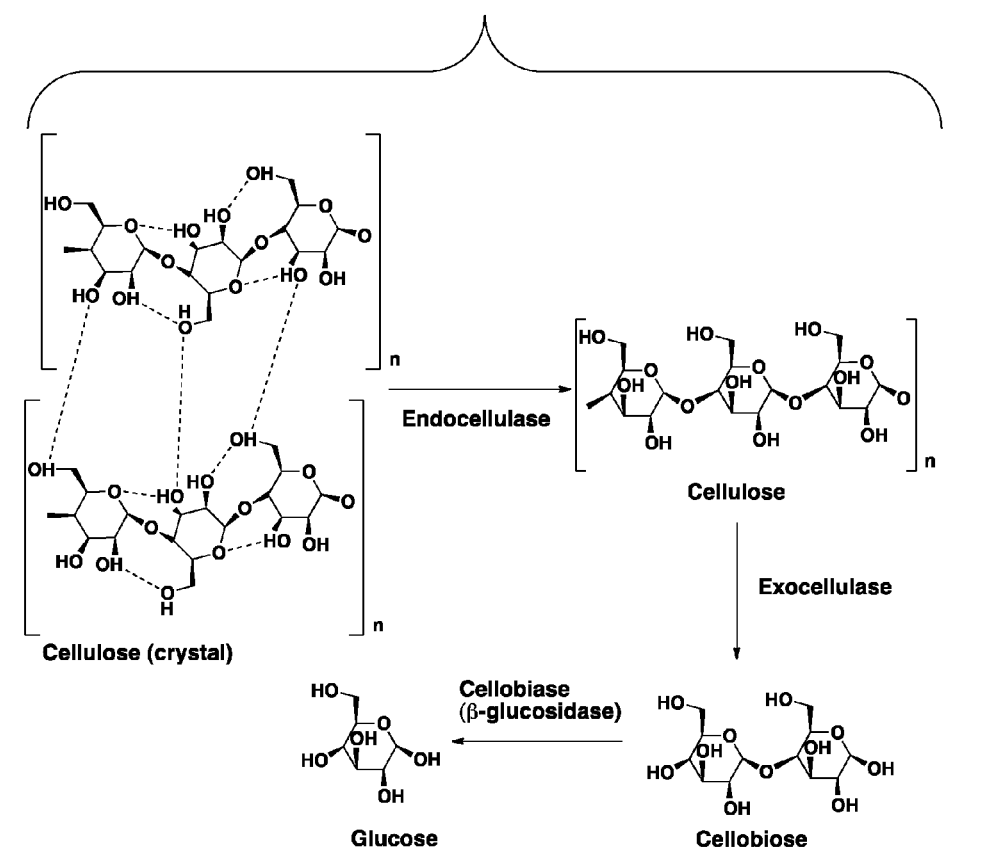
FIG. 1 is a diagram illustrating the enzymatic hydrolysis of cellulose and xylan to glucose and xylose respectively.

Generally, this invention relates to processes for converting a cellulosic, starchy or lignocellulosic feedstock to useful products, organic sugar derived products especially xylose conversion to furfural and furfural-derived products.

Cellulosic, hemicellulosic and lignocellulosic materials, such as biomass (e.g., plant biomass, animal biomass, paper, and municipal waste biomass), can be processed to a lower level of recalcitrance (if necessary) and converted into useful products such as those listed by way of example herein. Systems and processes are described herein that use readily abundant but often difficult to process cellulosic or lignocellulosic materials, e.g., municipal waste streams and waste paper streams, such as streams that include newspaper, kraft paper, corrugated paper or mixtures of these. Generally, if required, materials can be physically treated or processed using one or more of any of the methods described herein, such as mechanical treatment, chemical treatment, radiation, sonication, oxidation, pyrolysis and steam explosion.

In some cases, a manufacturing plant utilizing the processes described herein will obtain a variety of different feedstocks in the course of its operation. Some feedstocks may be relatively homogeneous in composition, for example a shipment of corn cobs, while other feedstocks may be of variable composition, for example municipal waste.

Feedstocks can include, for example, paper, paper products, wood, wood-related materials, particle board, grasses, rice hulls, bagasse, cotton, jute, hemp, flax, bamboo, wheat straw, sisal, abaca, straw, corn cobs, coconut hair, algae, seaweed, altered celluloses, e.g., cellulose acetate, regenerated cellulose, and the like, or mixtures of any of these.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

In order to process the feedstock to a form that can be readily converted the cellulose in the feedstock is hydrolyzed to low molecular carbohydrates, such as sugars, by a saccharifying agent, e.g., by an enzyme, a process referred to as saccharification. In some implementations, the saccharifying agent comprises an acid, e.g., a mineral acid. When an acid is used, co-products may be generated that are toxic to microorganisms, in which case the process can further include removing such co-products. Removal may be performed using an activated carbon, e.g., activated charcoal, or other suitable techniques.

The materials that include the cellulose are treated with the enzyme, e.g., by combining the material and the enzyme in a solvent, e.g., in an aqueous solution.

Enzymes and biomass-destroying organisms that break down biomass, such as the cellulose, hemicellulose and/or the lignin portions of the biomass, contain or manufacture various cellulolytic enzymes (cellulases), ligninases, xylanases, hemicellulases or various small molecule biomass-destroying metabolites. These enzymes may be a complex of enzymes that act synergistically to degrade crystalline cellulose, xylan or the lignin portions of biomass. Examples of cellulolytic enzymes include: endoglucanases, cellobiohydrolases, and cellobiases (β-glucosidases). Referring to FIG. 1, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose. In the case of hemicellulose, xylanase (e.g., hemicellulase) act on this biopolymer and release xylose as one of the possible products. Hemicellulose is a class of complex polysaccharides, often components in plant cell walls, including xylose units and includes xylan, glucuronoxylan, arabinoxylan, glucomannan and xyloglucan. Xylanase are a class of enzymes the degrade hemicellulose, e.g., degrade beta 1,4-xylan bonds, into xylose, thus breaking down the hemicellulose.

Cellulase and/or xylanase are capable of degrading biomass and may be of fungal or bacterial origin. Suitable enzymes include cellulases and xylanases (hemicellulases) from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cepha-*

*losporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, e.g., EP 458162) may be used.

The saccharification process can be partially or completely performed in a tank (e.g., a tank having a volume of at least 4000, 40,000, or 400,000 L) in a manufacturing plant, and/or can be partially or completely performed in transit, e.g., in a rail car, tanker truck, or in a supertanker or the hold of a ship. The time required for complete saccharification will depend on the process conditions and the feedstock and enzyme used. If saccharification is performed in a manufacturing plant under controlled conditions, the cellulose and hemicellulose may be substantially entirely converted to glucose and xylose in about 12-96 hours. If saccharification is performed partially or completely in transit, saccharification may take longer.

It is generally preferred that the tank contents be mixed during saccharification, e.g., using jet mixing as described in U.S. application Ser. No. 12/782,694, filed May 18, 2010; the full disclosure of which is incorporated by reference herein.

The addition of surfactants can enhance the rate of saccharification. Examples of surfactants include non-ionic surfactants, such as a polyethylene sorbitol ester Tween™ 20 or Tween™ 80, polyethylene glycol surfactants, ionic surfactants, or amphoteric surfactants.

It is generally preferred that the concentration of the resulting sugar (e.g. glucose and xylose) solution be relatively high, e.g., greater than 40%, or greater than 50, 60, 70, 80, 90 or even greater than 95% by weight. This reduces the volume to be shipped, and also inhibits microbial growth in the solution. However, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin, Virginiamycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

A relatively high concentration solution can be obtained by limiting the amount of water added to the feedstock with the enzyme. The concentration can be controlled, e.g., by controlling how much saccharification takes place. For example, concentration can be increased by adding more feedstock to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In some embodiments, the feedstock is processed to convert it to a convenient and concentrated solid material, e.g., in a powdered, granulate or particulate form. The concentrated material can be in a purified, or a raw, crude form. The concentrated form can have, for example, a total sugar concentration of between about 90 percent by weight and about 100 percent by weight, e.g., 92, 94, 96 or 98 percent by weight sugar. Such a form can be particularly cost effective to ship, e.g., to a bioprocessing facility, such as a biofuel manufacturing plant. Such a form can also be advantageous to store and handle, easier to manufacture and providing an option to the biorefinery as to which products to manufacture.

In some instances, the powdered, granulate or particulate material can also include one or more of the materials, e.g., additives or chemicals, described herein, such as a nutrient, a nitrogen source, e.g., urea or a peptone, a surfactant, an enzyme, or any microorganism described herein. In some instances, all materials needed for a bio-process are combined in the powdered, granulate or particulate material. Such a form can be a particularly convenient form for transporting to a remote bioprocessing facility, such as a remote biofuels manufacturing facility. Such a form can also be advantageous to store and handle.

In some instances, the powdered, granulate or particulate material (with or without added materials, such as additives and chemicals) can be treated by any of the physical treatments described herein. For example, irradiating the powdered, granulate or particulate material can increase its solubility and can sterilize the material so that a bioprocessing facility can integrate the material into their process directly as may be required.

In certain instances, the powdered, granulate or particulate material (with or without added materials, such as additives and chemicals) can be carried in a structure or a carrier for ease of transport, storage or handling. For example, the structure or carrier can include or incorporate a bag or liner, such as a degradable bag or liner. Such a form can be particularly useful for adding directly to a bioprocess system.

Figure 2:
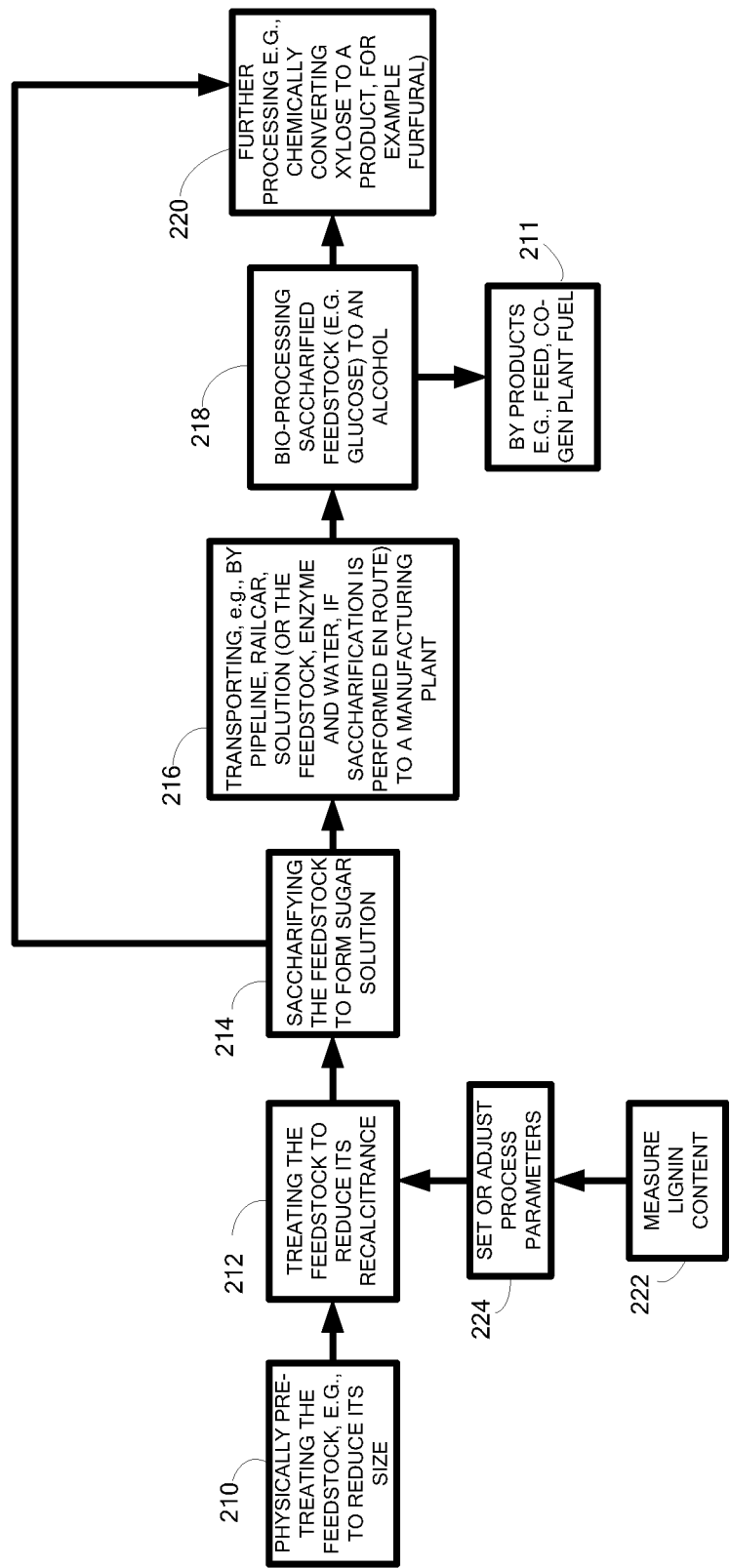
FIG. 2 is a flow diagram illustrating conversion of a feedstock to various products.

Referring to FIG. 2, a process for manufacturing a products from a biomass feedstock. For example, the biomass is converted by saccharification, bioprocessing and a chemical process, e.g., saccharification to xylose and glucose, fermentation of the glucose to an alcohol (e.g., ethanol), conversion of the un-fermented xylose to a product by a chemical reaction. The process, can include, for example, optionally mechanically treating the feedstock (step 210), before and/or after this treatment, optionally treating the feedstock with another physical treatment, for example irradiation, to further reduce its recalcitrance (step 212), saccharifying the feedstock to form a sugar solution (e.g., glucose and xylose) (step 214), transporting, e.g., by pipeline, railcar, truck or barge, the solution (or the feedstock, enzyme and water, if saccharification is performed en route) to a manufacturing plant (step 216), and then bio-processing the treated feedstock to produce a desired product such as an alcohol (step 218), further processing the unfermented xylose from the fermented solution to intermediates and products by chemical reactions, e.g., by steps including hydrogenation, dehydration, polymerization and/or oxidation (step 220). The individual steps of this process will be described in detail below. If desired, the steps of measuring lignin content (step 222) and setting or adjusting process parameters (step 224) can be performed at various stages of the process, for example just prior to the process step(s) used to change the structure of the feedstock, as shown. If these steps are included, the process parameters are adjusted to compensate for variability in the lignin content of the feedstock, as described in U.S. Pat. No. 8,415,122, the complete disclosure of which is incorporated herein by reference.

The manufacturing plant can be, for example, an existing starch-based or sugar-based ethanol plant or one that has been retrofitted by removing or decommissioning the equipment upstream from the bio-processing system (which in a typical ethanol plant generally includes grain receiving equipment, a hammer mill, a slurry mixer, cooking equipment and liquefaction equipment). Thus, the feedstock received by the plant is input directly into the fermentation equipment.

Biomass Materials

The biomass can be, e.g., a cellulosic, hemicellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, corn cobs, wheat, wheat straw, coconut hair; and materials high in-cellulose content, e.g., cotton. Feedstocks can be obtained from virgin scrap textile materials, e.g., remnants, post-consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307, 6,258,876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (II), and xylan (III) and which are derived from (β-glucose IV) and xylose respectively through condensation of β(1,4)-glycosidic bonds or by condensation of β-D-xylose units. This linkage contrasts itself with that for α(1,4)-glycosidic bonds present in starch and other carbohydrates.

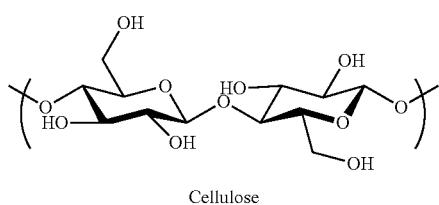

Cellulose

II

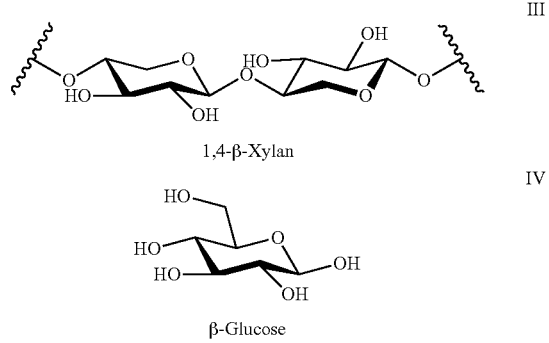

1,4-β-Xylan

III

β-Glucose

IV

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Physical Treatment

Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment methods is used, the methods can be applied at the same time or at different times. Other processes that change a molecular structure of a biomass feedstock may also be used, alone or in combination with the processes disclosed herein.

One or more of the treatment processes described below may be included in the recalcitrance reducing operating system discussed above. Alternatively, or in addition, other processes for reducing recalcitrance may be included.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the feedstock. The feedstock is sheared between stationary blades and rotating blades to provide a sheared material that passes through a screen, and is captured in a bin. The bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source is utilized to maintain the bin below nominal atmospheric pressure.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The cellulosic or lignocellulosic material can also be mechanically treated under a gas (such as a stream or atmosphere of gas other than air), e.g., oxygen or nitrogen, or steam.

If desired, lignin can be removed from any of the feedstock materials that include lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific characteristics such as, for example, specific maximum sizes, specific length-to-width, or specific surface areas ratios. Mechanical treatment can increase the rate of reactions or reduce the processing time required by opening up the materials and making them more accessible to processes and/or reagents, such as reagents in a solution. The bulk density of feedstocks can also be controlled using mechanical treatment. For example, in some embodiments, after mechanical treatment the material has a bulk density of less than 0.25 g/cm3, e.g., 0.20 g/cm3, 0.15 g/cm3, 0.10 g/cm3, 0.05 g/cm3 or less, e.g., 0.025 g/cm3. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material the fibers of the mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmett and Teller) surface areas are multi-point surface areas, and porosities are those determined by mercury porosimetry.

If the feedstock is a fibrous material the average length-to-diameter ratio of fibers of the mechanically treated material can be, e.g., greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the second fibrous material 14 can be, e.g., between about 5 µm and 50 µm, e.g., between about 10 µm and 30 µm.

In some embodiments, if the feedstock is a fibrous material a standard deviation of the fiber length of the mechanically treated material is less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the mechanically treated material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m²/g, greater than 35 m²/g, greater than 50 m²/g, greater than 60 m²/g, greater than 75 m²/g, greater than 100 m²/g m²/g, greater than 150 m²/g, greater than 200 m²/g, or even greater than 250 m²/g.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in WO 2008/073186.

Radiation Treatment

One or more radiation processing sequences can be used to process the feedstock, and to provide a structurally modified material which functions as input to further processing steps and/or sequences. Irradiation can, for example, reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components. In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized.

In one method, a first material that is or includes cellulose having a first number average molecular weight (first $M_N$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight (second $M_N$) lower than the first number average molecular weight. The second material (or the first and second material) can be combined with a microorganism (with or without enzyme treatment) that can utilize the second and/or first material or its constituent sugars or lignin to produce a fuel or other useful product that is or includes hydrogen, an alcohol (e.g., ethanol or butanol, such as n-, sec- or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing a microorganism and/or an enzyme. These properties make the second material more susceptible to chemical, enzymatic and/or biological attack relative to the first material, which can greatly improve the production rate and/or production level of a desired product, e.g., ethanol. Radiation can also sterilize the materials or any media needed to bioprocess the material.

In some embodiments, the second number average molecular weight (second $M_N$) is lower than the first number average molecular weight (first $M_N$) by more than about 10 percent, e.g., 15, 20, 25, 30, 35, 40, 50 percent, 60 percent, or even more than about 75 percent.

In some instances, the second material has cellulose that has as crystallinity (C2) that is lower than the crystallinity (C1) of the cellulose of the first material. For example, (C2) can be lower than (C1) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation (O2) that is higher than the level of oxidation (O1) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® E-beam Accelerator system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technetium, chromium, gallium, indium, iodine, iron, krypton, samarium, selenium, sodium, thallium, and xenon.

Sources of x rays include electron beam collision with metal targets, such as tungsten or molybdenum or alloys, or compact light sources, such as those produced commercially by Lyncean Technologies, Inc.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm. Optionally, the electrons having energies of 0.8 to 2 MeV may be used.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Optionally the electron energies can be 0.8 to 2 MeV. Typical electron beam irradiation device power can be 1 kW, 5 kW, 10 kW, 20 kW, 50 kW, 100 kW, 250 kW, or 500 kW. Additionally, electron beam irradiation device power can be 75 to 200 kW The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Electron beam irradiation devices from different instrument sources may be used. Multiple electron beam irradiation devices can be used to irradiate a biomass sample.

Ion Particle Beams

Particles heavier than electrons can be utilized to irradiate materials, such as carbohydrates or materials that include carbohydrates, e.g., cellulosic materials, lignocellulosic materials, starchy materials, or mixtures of any of these and others described herein. For example, protons, helium nuclei, argon ions, silicon ions, neon ions, carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed herein (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of H+, H−, He+, Ne+, Ar+, C+, C−, O+, O−, N+, N−, Si+, Si−, P+, P−, Na+, Ca+, and Fe+. In some embodiments, ion beams can include multiply-charged ions such as one or more of C2+, C3+, C4+, N3+, N5+, N3−, O2+, O2−, O22−, Si2+, Si4+, Si2−, and Si4−. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light Sonication One or more sonication processing sequences can be used to process materials from a wide variety of different sources to extract useful substances from the materials, and to provide partially degraded organic material (when organic materials are employed) which functions as input to further processing steps and/or sequences. Sonication can reduce the molecular weight and/or crystallinity of the materials, such as one or more of any of the materials described herein, e.g., one or more carbohydrate sources, such as cellulosic or lignocellulosic materials, or starchy materials.

In one method, a first material that includes cellulose having a first number average molecular weight (first $M_n$) is dispersed in a medium, such as water, and sonicated and/or otherwise cavitated, to provide a second material that includes cellulose having a second number average molecular weight (second $M_n$) lower than the first number average molecular weight. The second material (or the first and second material in certain embodiments) can be combined with a microorganism (with or without enzyme treatment) that can utilize the second and/or first material to produce a fuel that is or includes hydrogen, an alcohol, an organic acid, a hydrocarbon or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than 106 microorganisms/mL. These properties make the second material more susceptible to chemical, enzymatic, and/or microbial attack relative to the first material, which can greatly improve the production rate and/or production level of a desired product, e.g., ethanol. Sonication can also sterilize the materials, but should not be used while the microorganisms are supposed to be alive.

In some embodiments, the second number average molecular weight (second $M_n$) is lower than the first number average molecular weight (first $M_n$) by more than about 10 percent, e.g., 15, 20, 25, 30, 35, 40, 50 percent, 60 percent, or even more than about 75 percent.

In some instances, the second material has cellulose that has as crystallinity (C2) that is lower than the crystallinity (C1) of the cellulose of the first material. For example, (C2) can be lower than (C1) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation (O2) that is higher than the level of oxidation (O1) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis of the Feedstock Materials

One or more pyrolysis processing sequences can be used to process carbon-containing materials from a wide variety of different sources to extract useful substances from the materials, and to provide partially degraded materials which function as input to further processing steps and/or sequences.

In one example, a first material that includes cellulose having a first number average molecular weight (first $M_n$) is pyrolyzed, e.g., by heating the first material in a tube furnace (in the presence or absence of oxygen), to provide a second material that includes cellulose having a second number average molecular weight (second $M_N$) lower than the first number average molecular weight. The second material (or the first and second material in certain embodiments) is/are combined with a microorganism (with or without acid or enzymatic hydrolysis) that can utilize the second and/or first material to produce a fuel that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than 106 microorganisms/mL. These properties make the second material more susceptible to chemical, enzymatic and/or microbial attack relative to the first material, which can greatly improve the production rate and/or production level of a desired product, e.g., ethanol. Pyrolysis can also sterilize the first and second materials.

In some embodiments, the second number average molecular weight (second $M_n$) is lower than the first number average molecular weight (first $M_n$) by more than about 10 percent, e.g., 15, 20, 25, 30, 35, 40, 50 percent, 60 percent, or even more than about 75 percent.

In some instances, the second material has cellulose that has as crystallinity (C2) that is lower than the crystallinity (C1) of the cellulose of the first material. For example, (C2) can be lower than (C1) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation (O2) that is higher than the level of oxidation (O1) of the first material. A higher level of oxidation of the material can aid in its dispersability, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Oxidation of the Feedstock Materials

One or more oxidative processing sequences can be used to process carbon-containing materials from a wide variety of different sources to extract useful substances from the materials, and to provide partially degraded and/or altered material which functions as input to further processing steps and/or sequences.

In one method, a first material that includes cellulose having a first number average molecular weight (first $M_n$) and having a first oxygen content (O1) is oxidized, e.g., by heating the first material in a stream of air or oxygen-enriched air, to provide a second material that includes cellulose having a second number average molecular weight (second $M_n$) and having a second oxygen content (O2) higher than the first oxygen content (O1).

Such materials can also be combined with a solid and/or a liquid. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Fuels and coproducts are described in FIBROUS MATERIALS AND COMPOSITES," U.S. application Ser. No. 11/453,951, filed Jun. 15, 2006. The entire contents of each of the foregoing applications are incorporated herein by reference.

In some embodiments, the second number average molecular weight is not more 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight. The amount of reduction of molecular weight will depend upon the application. For example, in some preferred embodiments that provide composites, the second number average molecular weight is substantially the same as the first number average molecular weight. In other applications, such as making ethanol or another fuel or coproduct, a higher amount of molecular weight reduction is generally preferred.

In some embodiments in which the materials are used to make a fuel or a coproduct, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace.

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance employ Fenton or Fenton-type chemistry. Such methods are disclosed, for example, in U.S. application Ser. No. 12/639,289, filed Dec. 16, 2009, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Conditions can also include a contact period of between 2 and 12 hours, e.g., between 4 and 10 hours or between 5 and 8 hours. In some instances, conditions include not exceeding 300° C., e.g., not exceeding 250, 200, 150, 100 or 50° C. In special desirable instances, the temperature remains substantially ambient, e.g., at or about 20-25° C.

In some desirable embodiments, the one or more oxidants are applied to a first cellulosic or lignocellulosic material and the one or more compounds as a gas, such as by generating ozone in-situ by irradiating the first cellulosic or lignocellulosic material and the one or more compounds through air with a beam of particles, such as electrons.

In particular desirable embodiments, a first cellulosic or lignocellulosic material is firstly dispersed in water or an aqueous medium that includes the one or more compounds dispersed and/or dissolved therein, water is removed after a soak time (e.g., loose and free water is removed by filtration), and then the one or more oxidants are applied to the combination as a gas, such as by generating ozone in-situ by irradiating the first cellulosic or lignocellulosic and the one or more compounds through air with a beam of particles, such as electrons (e.g., each being accelerated by a potential difference of between 3 MeV and 10 MeV). Soaking can open up interior portions to oxidation.

In some embodiments, the mixture includes one or more compounds and one or more oxidants, and a mole ratio of the one or more compounds to the one or more oxidants is from about 1:1000 to about 1:25, such as from about 1:500 to about 1:25 or from about 1:100 to about 1:25.

In some desirable embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some desirable embodiments, the one or more oxidants are electrochemically-generated in-situ. For example, hydrogen peroxide and/or ozone can be electro-chemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, acid treatment (including concentrated and dilute acid treatment with mineral acids, such as sulfuric acid, hydrochloric acid and organic acids, such as trifluoroacetic acid), base treatment (e.g., treatment with lime or sodium hydroxide), UV treatment, screw extrusion treatment (see, e.g., U.S. patent application Ser. No. 12/417,723, filed Nov. 18, 2008, solvent treatment (e.g., treatment with ionic liquids) and freeze milling (see, e.g., U.S. Pat. No. 7,900,857)

Production of Fuels and/or Other Products by Bioprocessing

After one or more of the processing steps discussed above have been performed on the biomass, the complex carbohydrates contained in the cellulose and hemicellulose fractions can be processed into sugars using a saccharification process, as discussed above.

The resulting sugar solution can be converted into a variety of products by fermentation, such as alcohols, e.g., ethanol, or organic acids. The product obtained depends upon the microorganism utilized and the conditions under which the bioprocessing occurs. These steps can be performed, for example, utilizing the existing equipment of the corn-based ethanol manufacturing facility.

Generally, fermentation utilizes various microorganisms. The sugar solution produced by saccharification of lignocellulosic materials will generally contain xylose as well as glucose. It may be desirable to remove the xylose, e.g., by chromatography, as some commonly used microorganisms (e.g., yeasts) do not act on xylose. The xylose may be collected and utilized in the manufacture of other products, e.g., the sweetener Xylitol. The xylose may be removed prior to or after delivery of the sugar solution to the manufacturing facility where fermentation will be performed.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized. The microorganism can be an aerobe or an anaerobe. The microorganism can be a homofermentative microorganism (produces a single or a substantially single end product). The microorganism can be a homoacetogenic microorganism, a homolactic microorganism, a propionic acid bacterium, a butyric acid bacterium, a succinic acid bacterium or a 3-hydroxypropionic acid bacterium. The microorganism can be of a genus selected from the group Clostridium, Lactobacillus, Moorella, Thermoanaerobacter, Proprionibacterium, Propionispera, Anaerobiospirillum, and Bacteriodes. In specific instances, the microorganism can be Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus or Bacteriodes ruminicola. For example, the microorganism can be a recombinant microorganism engineered to produce a desired product, such as a recombinant Escherichia coli transformed with one or more genes capable of encoding proteins that direct the production of the desired product is used (see, e.g., U.S. Pat. No. 6,852,517, issued Feb. 8, 2005).

Carboxylic acid groups generally lower the pH of the fermentation solution, tending to inhibit fermentation with some microorganisms, such Pichia stipitis. Accordingly, it is in some cases desirable to add base and/or a buffer, before or during fermentation, to bring up the pH of the solution. For example, sodium hydroxide or lime can be added to the fermentation medium to elevate the pH of the medium to range that is optimum for the microorganism utilized.

Fermentation is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost. For example, in many instances, the growth medium itself or components of the growth medium can be treated with a radiation dose of less than 5 Mrad, such as less than 4, 3, 2 or 1 Mrad. In specific instances, the growth medium is treated with a dose of between about 1 and 3 Mrad.

Products by Chemical Reactions

Figure 3:
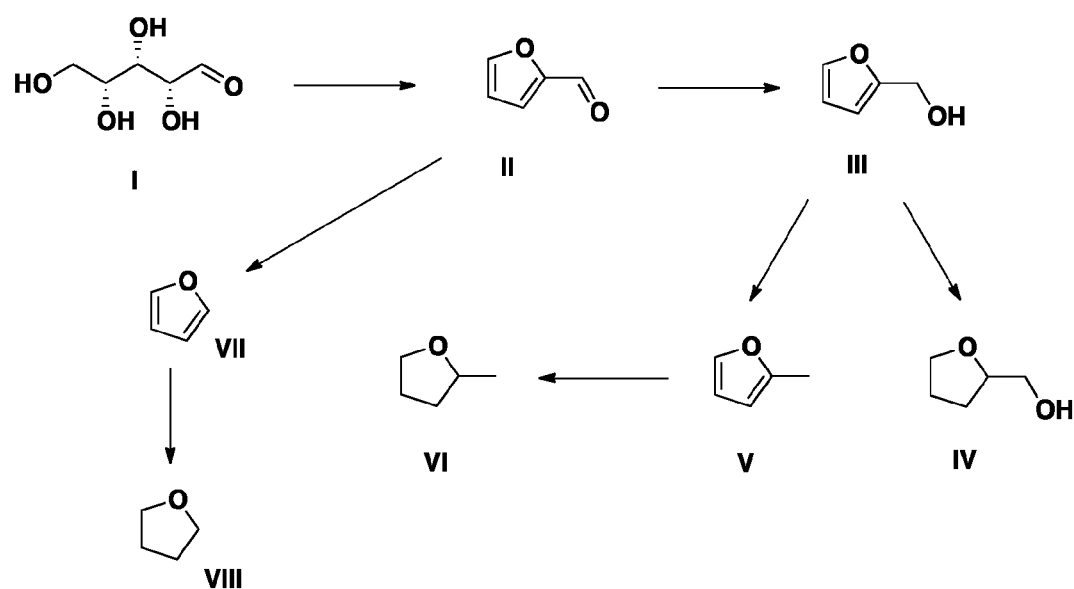
FIG. 3 is a reaction scheme showing possible organic intermediates or products derived from a sugar.

FIG. 3 shows various transformation of xylose (3a) in its open chain aldehyde form to products. Chemical transformations using, for example, catalysts are useful to convert sugars (e.g., xylose) derived from biomass material as described herein into useful organic products. The products can be directly converted to a product (e.g., furfural 3b) or can be converted through various intermediates as depicted in FIG. 3. Prior to conversion the, sugar (e.g., xylose) can be isolated, concentrated, and/or purified from the saccharified biomass using various methods such as distillation, crystallization, precipitation, chromatography (e.g., simulated moving bed chromatography), centrifugation, settling, sedimentation, floatation, fermentation (e.g., fermentation of other sugars such as glucose to a greater degree than the xylose) or combinations of these and/or other methods.

Chemical conversions can be performed in the same tank as the saccharification (e.g., in situ right after saccharification) or transferred (optionally with a purification step) to a second tank for chemical reaction. For example the tank for the chemical reaction can be equipped with temperature control units, mixing units, may be made to withstand corrosive or dissolving solvents, made to withstand higher than atmospheric pressure. These chemical conversions can also be done in a continuous fashion (e.g., using a tube reactor, continuous stirred tank reactor) or semi-continuous fashion.

Examples of chemical conversion of xylose to furfural and subsequent products is shown if FIG. 3. While several of the products do not have any carbon atom that has stereochemistry, products 3d and 3f do have stereocenters. The chemistries envisaged here can lead to pure stereoisomers or D,L mixtures that could be resolved.

The chemical conversion of xylose (3a) to methytetrahydrofuran (3f) can be done in several steps. In a first step xylose (3a) is dehydrated and cyclization to furfural (3b) alternatively called furancarboxaldehyde which is an oily, colorless heterocyclic aldehyde. Several catalyst systems can transform xylose to furfural successfully. Some possible acidic systems are Zeolite acidified with $H_3PO_4/H_2SO_4$; Sulfonic acid, Silica surface grafted; 1-Methylimidazole, i-BuC(=O)Me; KI, KCl; 1-alkyl-3-methylimidazolium ionic liquids; NaCl, HCl, $SiO_2$, Zeolite Beta, Sulfonic acid functionalized mesoporous silica MCM-41; perfluorinated sulfonic acid resins (Nafion®), acidic clays, $FeCl_3$, NaCl; Mesoporous silica supported; SBA-15 supported sulfonic acid, $SiO_2$, $H_2SO_4$; Tetraethyl orthosilicate, 3-(mercaptopropyl) trimethoxy silane, $LaCl_3$; Microporous silicoaluminophosphate; $ZrO_2$, Tungstate; LSC resin; $Al_2O_3$, tungstate; $TiO_2$ sulfonated; $V_2O_5$, $H_3PO_4$; $ZrO_2$, $Al_2O_3$, $(NH_4)SO_4$; $SiO_2$, $MgCl_2$; HCl, Microwave irradiation; Amberlyst 15; $Cs_2CO_3$, $SiO_2$. These reactions can be performed under higher temperatures and/or high pressure.

Furfural is used as a solvent for refining lubricating oils, as a fungicide and weed killer Furfural is also a chemical intermediate in the production of methyltetrahydrofuran (3f) which is an important industrial solvent. In addition, furfural (3b) can serve as a building block for other potential transportation fuels. Furfural is an important renewable, non-petroleum based, chemical feedstock. It is highly regarded for its thermosetting properties, physical strength and corrosion resistance. It is consumed by the chemical industry as an intermediate product in synthesizing chemical products such as nylon, lubricants, solvents, adhesives, medicines and plastics.

Furfural is also a chemical intermediate to furfuryl alcohol since reduction of the aldehyde group of furfural provides furfuryl alcohol (3c). Furfuryl alcohol is also a useful chemical intermediate and can be dearomatized to tetrahydrofurfuryl alcohol (3d). Some of the industrial processes are listed below:

In a two-step process, biomass (e.g., plant materials) containing xylose is mixed with an acid (e.g., dilute sulphuric acid) or a saccharifying enzyme, producing sugars including xylose. The xylose is cyclohydrated losing three moles of water to furfural in the second step, e.g., with an acid (e.g., dilute sulphuric acid optionally from the first step). The product can be recovered by steam distillation from a mixture of acid and undigested biomass.

Furfural (3b) is a versatile chemical intermediate and can be used to make other furan chemicals, such as furoic acid, via oxidation, and furan (3g) itself via palladium catalyzed vapor phase decarbonylation. Furfuryl alcohol (3c) can be manufactured by the catalytic reduction of furfural. Reduction of the furfural aldehyde group (3b) can yield furfuryl alcohol. For example, the aldehyde can be reduced by using $NaBH_4$ in MeOH in one hour with (e.g., yielding greater than 10% product, e.g., greater than 20%, greater than 30%, greater than 40%, greater than 50%, greater than 60%, greater than 70%, greater than 80%). Other reactants that can be used for this transformation include, $FeCl_3$, $ZnCl_2$; $NiCl_2$, $Al_2O_3$; Pt, $TiO_2$, $SiO_2$; $NH^{4+}.HCO^{2-}$, Ni; [RhCl(COD)]$_2$; CuO, $Cr_2O_3$, $SiO_2$.

Furfuryl alcohol (3c), also called 2-furylmethanol or 2-furancarbinol (3c), is an organic compound containing a furan substitute hydroxymethyl group. It is a clear colorless liquid when pure, but becomes amber colored upon prolonged standing. It possesses a faint burning odor and a bitter taste. It is miscible with but unstable in water. It is soluble in common organic solvents. Upon treatment with acids, heat and/or catalysts, furfuryl alcohol can be made to polymerize into a resin, poly(furfuryl alcohol). It also can be used as a solvent and as an ingredient in the manufacture of various chemical products such as foundry resins, adhesives, and wetting agents.

Furfuryl alcohol (3c) has been used in rocketry as a fuel, which ignites with white fuming nitric acid or red fuming nitric acid oxidizer. Because of its low molecular weight, furfuryl alcohol (3c) can impregnate the cells of wood, where it can be polymerized and bonded with the wood by heat, radiation, and/or catalysts or additional reactants (e.g., by the methods disclosed in U.S. Pat. No. 7,846,295 the full disclosure incorporated herein by reference). The treated wood has improved moisture stability, dimensional stability, hardness, microbial decay resistance and insect resistance; catalysts can include zinc chloride, citric or formic acid, or borates.

Dearomatization of furfuryl alcohol (3c) to tetrahydrofurfuryl alcohol (3d) can be performed using several metal catalysts under high pressures (e.g., between 10 and 8000 psi) and temperatures (e.g., from 50 to 400° C.). For example, catalysts can be selected from: Hectorite supported Ru nanoparticles; nickel boride/$SiO_2$; Skeleton Ni; L-Serine, Alginic acid, platinum complex; $Na_2O$, ZnO, NiO, $Al_2O_3$; Ni, Al, Mo, Si, Ca; Rh-PPh$_3$ complex; $RuO_2$; Ru; Ru/$TiO_2$; Al/Ni alloy; nickel boride, nickel/cobalt boride; NiO, amongst others. The hydrogenation reactions take from minutes (or hours) to a day (or several days). Tetrahydrofurfuryl alcohol is a hygroscopic, colorless liquid, miscible with water; used as a solvent for resins, in leather dyes, and in nylon. Tetrahydrofurfuryl alcohol can be used as a non-hazardous solvent in agricultural formulations and as an adjuvant to help herbicides penetrate the leaf structure. Dihydropyran can be prepared by the dehydration of tetrahydrofurfuryl alcohol over alumina at 300-400° C.

2-Methyltetrahydrofuran (3f) is an organic compound with the molecular formula $CH_3C_4H_7O$. It is a highly flammable mobile liquid. It is mainly used as a replacement for THF in specialized applications for its better performance in those applications, e.g., to obtain higher reaction temperatures, or easier separations due to the solubility, changed acidity and changed donor properties of the ring oxygen of the 2-methyltetrahydrofuran. It also is used in the electrolyte formulation for secondary lithium electrodes and as a component in alternative fuels. It is a valued solvent for low temperature reactions. 2-Methyltetrahydrofuran forms a glass, which does not crystallize, and is frequently used as a solvent for spectroscopic studies at −196° C. Methyltetrahydrofuran has a stereocenter alpha to the oxygen. The methyltetrahydrofuran produced by these chemistries may be a 50:50 mixture of stereoisomers or enriched in either enantiomer.

Other common uses of 2-methyltetrahydrofuran is as a solvent for Grignard reagents used in organometallic and biphasic chemical processes, because of the oxygen atom's ability to coordinate to the magnesium ion component of the Grignard reagent, or to azeotropically dry products. The use of 2-methyltetrahydrofuran provides very clean organic-water phase separations. It is a popular, but costlier substitute for tetrahydrofuran.

2-Methyltetrahydrofuran has been approved by the United States Department of Energy as an additive to gasoline. Furfural and other partially hydrogenated/reduced furyl compounds between it and 2-methyltetrahydrofuran (furfuryl alcohol, methylfuran, tetrahydrofuryl alcohol) have a tendency to polymerize and are quite volatile. 2-methyltetrahydrofuran itself, however, is more stable and less volatile, and thus is suitable for use as a motor fuel.

2-Methyltetrahydrofuran has one stereocenter, so it exists in two enantiomeric forms. In some processes involving hydrogenation a racemic mixture of the two enantiomers is formed. The asymmetric synthesis of (S)-(+)-2-methyltetrahydrofuran can be achieved by using chiral catalytic hydrogenation, e.g., using supported catalysts such as wool-rhodium complex.

The conversion of 3c to 3e involves hydrogenolysis. 3e can be converted to 3f by vapor phase hydrogenation using Raney Ni under 200° C.

Furfural (3b) can be catalytically converted to Furan (3g) by metal complexes. For examples, the reactions can be made to proceed via metal-acyl hydrides. Cu/Mo fixed bed complex can catalyze this conversion under high pressures and temperatures (e.g., between 10 and 20000 psi and 50 to 400° C.) with continuous flow of hydrogen. Catalyst complexes of Pd and Ni have also been used but they have proven to be less selective (leading to ring opening and C4 compounds). The hydrogenation of Furan (3g) to tetrahydrofuran (3h) can be performed under high pressure and temperature under hydrogen using metal based catalysts such as Raney Ni, Ru and Pt The furfural-derived products can be the product of a multiple step reaction scheme. The intermediates along the reaction scheme may be isolated before subsequent reactions. For example, the furfural can be isolated and purified prior to conversion of furfuryl alcohol.

EXAMPLES

Unless otherwise noted the chemicals were obtained from Alfa Chemical, Kings Point N.Y.; Sigma Aldrich Chemical, St Louis, Mo.

Example I

Xylose Conversion to Furfural with Acetic Acid

To a 1-Liter pressure vessel equipped with a vent condenser (Parr stainless steel reactor, Parr Instrument Company, Moline Ill.) 20 grams of xylose, 0.2 mL of glacial acetic acid and 400 mL of water was added. The vessel was heated to 185° C. and liquids distilled from the reactor. The total heating time was two hours. Most of the furfural was recovered from the distillate. The furfural yield was determined by gas chromatography to be 39 percent.

Example II

Xylose Conversion to Furfural

To a 1-Liter pressure vessel equipped with a vent condenser (Parr stainless steel reactor, Parr Instrument Company, Moline Ill.) 50 grams of xylose, and 500 mL of water was added. The reactor was heated to 185° C., agitated at 350 rpm and the pressure was 145 psig. The furfural yield was 45 percent.

Example III

Xylose Conversion to Furfural, Calcium Chloride Added

To a 1-Liter pressure vessel equipped (Parr stainless steel reactor, Parr Instrument Company, Moline Ill.) 30 grams of xylose (from Cascade Analytical Reagents and Biochemical, Corvallis, Oreg.), 300 mL of methyltetrahydrofuran, calcium chloride, 30 grams and 150 mL of water was added. The reactor was heated to 200° C. for four hours. The furfural yield was 55 percent.

Example IV

Xylose Conversion to Furfural; Continuous Processing

Xylose was dissolved in water at 0.66 moles/liter. This solution was pumped through a heated tubular reactor. At 180° C. the furfural yield was less than 5 percent. At 200° C. the yield was 13% at a 10 minute residence time. At 220° C. at a 10 min residence time reached 40%.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (e.g., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing furfuryl alcohol comprising:
    irradiating biomass to reduce the recalcitrance of the biomass;
    saccharifying the irradiated biomass with one or more enzymes to produce a first sugar composition comprising xylose and glucose;
    fermenting the first sugar composition to produce a second sugar composition comprising xylose and glucose, wherein the concentration of xylose in the second sugar composition is increased relative to the first sugar composition;
    isolating the xylose from the second sugar composition by simulated moving bed chromatography;
    converting the isolated xylose to furfural; and
    reducing the furfural to furfuryl alcohol.

2. The method of claim 1 wherein the biomass comprises one or more of paper, paper product, wood, wood-related material, particle board, grass, rice hulls, bagasse, cotton, jute, hemp, flax, bamboo, wheat straw, sisal, abaca, straw, corn cobs, corn stover, coconut hair, algae, seaweed, altered cellulose, regenerated cellulose, microbial material, municipal waste, waste from paper processing, newspaper, kraft paper, corrugated paper, cotton, rags, and animal waste.

3. The method of claim 1 wherein the biomass is densified before irradiating.

4. The method of claim 1 further comprising treating the biomass to reduce its recalcitrance, before or after irradiating, with one or more of mechanically treating, sonicating, pyrolyzing, oxidizing, steam exploding, and chemically treating.

5. The method of claim 1 wherein the biomass has been irradiated with one or more of microwave energy, ultraviolet rays, infrared radiation and ionizing radiation.

6. The method of claim 1 wherein the biomass has been irradiated with one or more of alpha particles, protons, gamma rays and X-rays.

7. The method of claim 1 wherein the biomass has been irradiated with ions heavier than electrons.

8. The method of claim 1 wherein the biomass has been irradiated with ionizing radiation delivered by electron beam.

9. The method of claim 8 wherein the ionizing radiation is delivered at a dosage that is between 10 Mrad and 200 Mrad.

10. The method of claim 8 wherein the electron beam has a power between 0.5 and 10 MeV.

11. The method of claim 1 wherein the biomass has been irradiated with two or more radiation sources.

12. The method of claim 1 wherein the biomass has been treated to reduce its recalcitrance, before or after irradiating, by sonicating in an oxidizing medium.

13. The method of claim 1 further comprising partially or completely saccharifying the biomass during transporting to a manufacturing plant.

14. The method of claim 1 wherein the biomass has been saccharified partially or completely in a tank.

15. The method of claim 14 wherein the contents of the tank are jet mixed.

16. The method of claim 14 wherein conversion of the xylose to furfural occurs in the tank.

17. The method of claim 16 wherein conversion of the xylose to furfural occurs in a continuous process.

18. The method of claim 1 wherein the one or more enzymes comprise a ligninase, a xylanase, a hemicellulase, an endoglucanase, a cellobiohydrolase, or a beta-glucosidase.

19. The method of claim 1 wherein the one or more enzymes comprise an enzyme complex including xylanase.

20. The method of claim 1 wherein the sugars are at a concentration of at least 40% by weight.

21. The method of claim 1 further comprising isolating the glucose.

22. The method of claim 1 further comprising isolating the furfuryl alcohol.

23. The method of claim 1 wherein conversion of the xylose to furfural is catalyzed by a Lewis acid.

24. The method of claim 1 further comprising measuring the lignin content of the biomass.

* * * * *